July 4, 1961 A. M. SHAMMARELLO Plant Pat. 2,068
AZALEA PLANT
Filed March 17, 1960
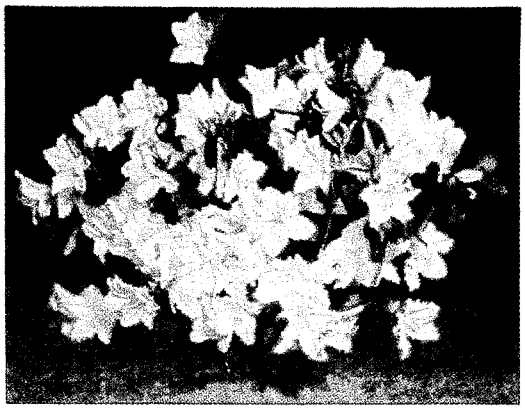
INVENTOR.
A. M. Shammarello
BY Robb & Robb
Attorneys United States Patent Office Plant Pat. 2,068
Patented July 4, 1961

2,068
AZALEA PLANT

Anthony M. Shammarello, 4590 Monticello Blvd., South Euclid, Ohio

Filed Mar. 17, 1960, Ser. No. 15,775
1 Claim. (Cl. 47—60)

My present invention comprises a new and distinct variety of azalea plant, the result of crossing the variety Azalea Poukhanense with the variety Ledifolia Alba, both parents being unpatented varieties.

The principal object of my invention was to produce a new variety of azalea plant having a better habit of growth, greater hardiness, and white flowers of good character.

The foregoing objective has been attained in my new variety which is characterized by its bushy habit of growth, hardy plant, and hardy buds, its large, white, and frilled bloom, and its retention of more foliage throughout the winter.

The plants of my new variety are bushier and have denser foliage and larger flowers than Azalea Poukhanense, being in these respects more similar to Ledifolia Alba. My new variety is much more hardy than Ledifolia Alba, being in this respect more like Poukhanense.

The hardiness of the plant and buds of my new variety is indicated by the fact that they were not in any way adversely affected by winter temperatures of minus twelve degrees (−12°) Fahrenheit.

The flowers of my new variety are almost pure white and the margins of the lobes are frilled and thus the flowers are unusually attractive.

The plants of my new variety have the characteristic of retaining substantially more foliage through the winter than Azalea Poukhanense thus making the plants more attractive throughout the year.

My new variety has been found to retain its distinctive characteristics through successive asexual reproduction. Such asexual reproduction has been accomplished by means of cuttings in the vicinity of South Euclid, Ohio.

The accompanying drawing forming a part hereof shows a typical plant of my new variety of azalea.

The following is a detailed description of my new variety of azalea plant:

Color references are to Nickerson Color Fan as published by Munsell Color Company.

Parentage: Azalea Poukhanense (female) × Ledifolia Alba (male).

Habit of growth: Medium, low-branched, upright and spreading.

Young shoots: Stems—color 2.5GY 6/8 strong yellow green.

Mature shoots: Stems—color 7.5YR 4/5 moderate brown.

Foliage:

*Color of young leaves.*—5GY 5/6 moderate yellow green.

*Color of mature leaves.*—5GY 4/3 moderate olive green.

*Color of hair on leaf.*—On surface of leaf—white N–9 Munsell Neutral Value scale. On underside of leaf—white N–9 Munsell Neutral Value scale.

*Arrangement of leaves.*—In a spiral.

*Form of leaves.*—Elliptical.

*Size of leaves.*—2 to 2½ inches long—1 to 1¼ inches wide.

Flower: Season of bloom—midseason—about May 18th.

*Type.*—Single.

*Borne.*—Usually 3 in a cluster.

*Size of petal spread.*—2 to 2½ inches.

*Color.*—White N9.5 Munsell Neutral Value scale.

*Stamens.*—Nine; color—white N–9 Munsell Neutral Value scale.

*Form.*—Five petals—margins of lobes frilled.

*Blotch.*—2.5GY 9/8 brilliant yellow green.

Hardiness: Plant and buds withstood temperatures of −12° Fahrenheit.

I claim:

A new and distinct variety of azalea plant substantially as shown and described, characterized by its bushy habit of growth, hardy plant, and hardy buds, its large, white, and frilled bloom, and its retention of more foliage throughout the winter than Azalea Poukhanense.

No references cited.